(12) United States Patent
Leite

(10) Patent No.: US 11,363,868 B1
(45) Date of Patent: Jun. 21, 2022

(54) CURL-HAIR DEFINING METHOD

(71) Applicant: Thalita Leite, Weymouth, MA (US)

(72) Inventor: Thalita Leite, Weymouth, MA (US)

( * ) Notice: Subject to any disclaimer, the term of this patent is extended or adjusted under 35 U.S.C. 154(b) by 0 days.

(21) Appl. No.: 17/374,101

(22) Filed: Jul. 13, 2021

(51) Int. Cl.
| | | |
|---|---|---|
| *A61Q 5/00* | (2006.01) | |
| *A61Q 5/04* | (2006.01) | |
| *A45D 7/06* | (2006.01) | |
| *A45D 19/00* | (2006.01) | |
| *A61Q 5/12* | (2006.01) | |
| *A61K 8/44* | (2006.01) | |
| *A61K 8/365* | (2006.01) | |

(52) U.S. Cl.
CPC ............. *A45D 7/06* (2013.01); *A45D 19/005* (2021.01); *A61K 8/365* (2013.01); *A61K 8/447* (2013.01); *A61Q 5/04* (2013.01); *A61Q 5/12* (2013.01)

(58) Field of Classification Search
None
See application file for complete search history.

(56) References Cited

U.S. PATENT DOCUMENTS

| | | |
|---|---|---|
| 6,517,822 B1 | 2/2003 | Buck |
| 8,114,392 B2 | 2/2012 | Muller et al. |
| 8,540,975 B2 | 9/2013 | Verboom et al. |
| 8,591,872 B2 | 11/2013 | Singer et al. |
| 9,283,157 B2 | 3/2016 | Savaides et al. |
| 2007/0280896 A1 | 12/2007 | Nguyen et al. |
| 2009/0126756 A1 | 5/2009 | Syed et al. |
| 2015/0313832 A1 | 11/2015 | Hilvert et al. |
| 2015/0374604 A1* | 12/2015 | Kadir ................. A61Q 5/06 549/230 |
| 2016/0228342 A1* | 8/2016 | Rose ................... A61Q 5/12 |
| 2016/0235638 A1* | 8/2016 | Rose ................... A61K 8/342 |
| 2017/0143603 A1 | 5/2017 | Mannozzi |
| 2017/0157011 A1* | 6/2017 | Punyani ............... A61K 8/042 |
| 2019/0038534 A1* | 2/2019 | Consoli ............... A61Q 5/10 |
| 2020/0022903 A1* | 1/2020 | Syed .................... C08G 77/26 |
| 2021/0283028 A1* | 9/2021 | Nagasaki ............ A61Q 5/00 |

FOREIGN PATENT DOCUMENTS

| | | |
|---|---|---|
| EP | 2723310 B1 | 7/2016 |
| WO | 2011074144 A1 | 6/2011 |
| WO | 2015200778 A1 | 12/2015 |

* cited by examiner

*Primary Examiner* — Jyothsna A Venkat
(74) *Attorney, Agent, or Firm* — Law Office of Ilya Libenzon

(57) ABSTRACT

A method of treating hair to reduce frizz involving the following steps: (i) prewashing the hair with water, (ii) applying a frizz reducing product to the hair using at least one of a brush and a spray, (iii) drying the hair in air, (iv) rinsing the hair with water, (v) drying the hair, (vi) applying to the hair a flat iron, and (vii) rinsing the hair with water. The frizz reducing agent used to treat hair is glyoxylic acid. The specific temperature the flat iron is set will depend on the specific hair type and degree of frizz.

3 Claims, 11 Drawing Sheets

Types of Hair

Curly

Coily

Wavy

Loose

14

Low Degree of Frizz

15

High Degree of Frizz

Before

7

Treatment →

After

8

7

Treatment →

8

CURL-HAIR DEFINING METHOD

TECHNICAL FIELD

Embodiments disclosed herein relate generally to a method of treating and defining different types of hair including wavy, curly and coily hair, and more particularly a method that reduces frizz using a frizz reducing buffer, temperature, and a series of treatment steps.

BACKGROUND ART

Frizzy hair occurs when the cuticle layer of hair rises. Some factors that cause frizz include the environment, diameter of the hair fiber itself, the level of a curl, and the amount of damage. Frizzy hair can also be characterized by having unruly strands shaped differently than the most concentrated hair strand type. Some wavy, curly or coily hair is defined, but some have mixed curl patterns, which can cause frizzy hair. Frizzy hair is often characterized as having a zigzag shape, as opposed to an S-pattern. Using the hair-curl defining method of the present invention most of these issued can be minimized. It is important to notice that frizzy hair in itself is not damaged hair but rather a product of generics, possessing inherited characteristics such as having unruly strands, or unruly hair.

A number of frizz products exist that help the cuticle to lay flat. However, frizz can still occur when the appropriate products or brushing techniques are not used. The incorrect shampoo or brushing technique can result in opening up cuticles even when the correct frizz product is applied. Many different treatments exist that help reduce the effects of open cuticles, but they are expensive and time consuming. In addition, many treatments do not last long, some only a few days. Moreover, this commercially-available treatments are not adequately designed to accommodate different types of hair or their combinations, especially frizzy hair, which is not defined hair characterized in having raised cuticles and strands that wave and curl in different directions. It becomes especially pronounced in cases when hair contains a mix of different hair patterns per square inch. For instance, wherein type 2B hair is having a mixture of type 4A and type 4B hair strands, which are not unified. There is no product in the market that is effective in unifying and defining those strands of hair together.

Therefore, there is a need for an inexpensive and effective curl-hair defining method that makes hair curls looser, more defined, unified, manageable, healthier, less porous, shinier, and will maintain the results for a very long time, in some instances, resulting in a permanent solution, wherein once treated the hair does not return into its virgin natural state anymore.

SUMMARY OF THE EMBODIMENTS

The present invention provides a method for reducing frizz found in different types of hair by applying a combination of hair products, brushing techniques, and a flat iron set at different temperatures. Frizzy hair is a result of the hair cuticles opening up causing hair to appear rough and unmanageable, or when hair strands are going in opposite direction or in a zigzag pattern. When the frizz reducing product, such as glyoxylic acid, is applied followed by the application of a flat iron set at a specific temperature range, the hair cuticles close and lie flat giving the appearance of smooth and unified hair, still controlling the hair's bounce, overall s-shape. In some instances, the frizz reducing product can be glyoxyloyl carbocysteine. It's central to the method of the present invention to treat hair with a frizz reducing product by appling a flat iron at specific temperatures for each curl/hair type.

The disclosed method of treating hair has the following steps: (i) prewashing the hair with water; (ii) applying a frizz reducing product to the hair using at least one of a brush and a spray, (iii) drying the hair in air, (iv) rinsing the hair with water again, (v) drying the hair, (vi) applying a flat iron with a specific temperature corresponding to at least one of specific hair type and degree of frizz; and (vii) rinsing the hair again; and is performed twice (round one and round two). The temperature of the flat iron will be higher in round one and lowered in round two, this applies for all types of hair. In some instances, coily and curly hair can be treated with the same temperature in first and second round according to some methods of the present invention.

Glyoxylic acid is an important building block for many organic molecules and is used in the production of agrochemicals, aromas, cosmetic ingredients, pharmaceutical intermediates and polymers because it acts as a neutralizing agent. In hair, glyoxylic acid has semi-permanent straightening properties and does not damage hair or cause scalp irritation. It's ability to smoothen wavy and curly hair makes it the ideal agent to improve hair manageability and allows for a shiny silk appearance in hair. In a preferred embodiment, glyoxylic acid is used to reduce frizz in hair.

A flat iron will be used to reduce frizz. The high temperature of the flat iron causes a temporary straightening of the hair by breaking the hydrogen bonds in the hair keratin. When applied with a treatment of glyoxylic acid, natural curls are softened due to the neutralizing agent. The frizzy strands loosen and join together to create defined waves and curls.

Other aspects, embodiments and features of the method will become apparent from the following detailed description when considered in conjunction with the accompanying figures. The accompanying figures are for schematic purposes and are not intended to be drawn to scale. In the figures, each identical or substantially similar component that is illustrated in various figures is represented by a single numeral or notation. For purposes of clarity, not every component is labeled in every figure. Nor is every component of each embodiment of the cover and method shown where illustration is not necessary to allow those of ordinary skill in the art to understand the cover and method.

BRIEF DESCRIPTION OF THE DRAWINGS

The preceding summary, as well as the following detailed description of the disclosed device and method, will be better understood when read in conjunction with the attached drawings. It should be understood, however, that neither the device nor the method is limited to the precise arrangements and instrumentalities shown.

DETAILED DESCRIPTION OF SPECIFIC EMBODIMENTS

A person skilled in the art will appreciate that the methods disclosed herein can be implemented using any type of hair and any degree of fizz. The present invention provides a method for reducing frizz found in different types of hair by applying a combination of hair products, brushing techniques, and different flat iron temperatures.

Figure 1:
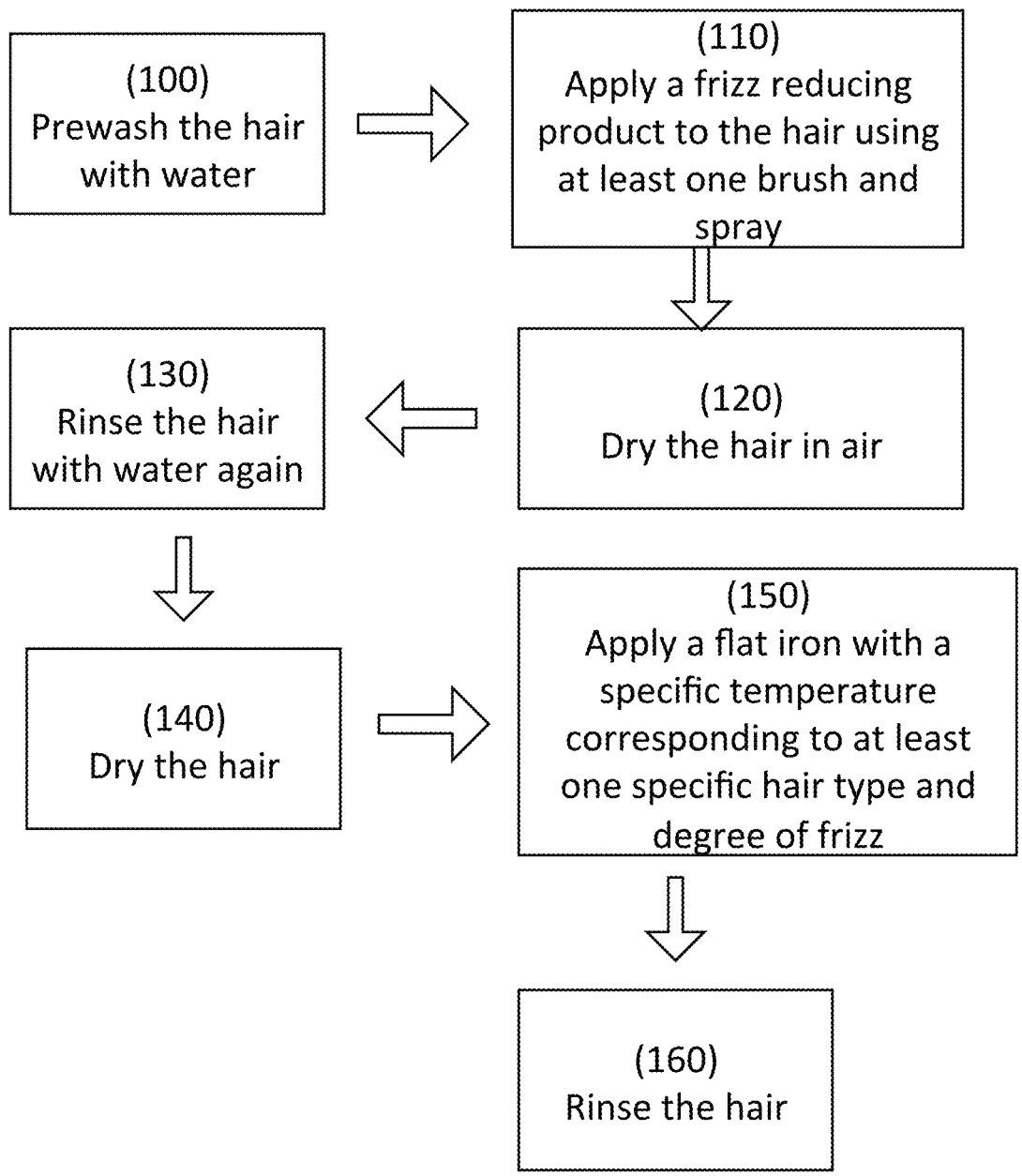
FIG. 1 depicts a flow chart which illustrates a series of steps for the first round of treatment to maximize the reduction of frizz in hair.

Referring now to the drawings in detail, the disclosed method for treating hair as seen in FIG. 1 has the following steps: (100) prewashing the hair with water; (110) applying a frizz reducing product to the hair using at least one of a brush and a spray, (120) drying the hair in air, (130) rinsing the hair with water again, (140) drying the hair, (150) applying a flat iron with a specific temperature corresponding to at least one of specific hair type and degree of frizz; and (160) rinsing the hair again. The prewashing step will be done with shampoo or a conditioner, or both in order to loosen the hair for the application of the frizz reducing product.

Step (110) applies a frizz reducing product in conjunction with at least one brush and one spray. In most instances the frizz reducing product, Glyoxylic acid, will be applied to improve hair manageability by smoothening hair.

In some embodiments the frizz reducing product will be another agent with similar properties as glyoxylic acid and also falls within a pH range of 3-6, and in some instances within a pH range of 4-6. The frizz reducing product is more concentrated for curly and coily hair and less concentrated for wavy hair. In some instances the pH can be in the range of 1-2, and in some other instances 0.08-3.0.

When hair is dried using air in step (120), the duration hair is dried will be between 10 minutes and 20 minutes, in some instances up to 50 minutes, and will depend on the type of hair being treated. Once the hair is dried, the hair will once again be rinsed with water as seen in step (130) and dried again for 10 to 20 minutes in step (140), in some instances up to 50 minutes.

A flat iron will be used to reduce frizz in step (150) by resting a strand of hair in between the heated sides of the flat iron and moving the flat iron down. A unique aspect of this method is the manner that hair is parted to treat separate strands. Each strand to be treated is approximately 1.27 cm to 10.16 cm in width ($D_1$, $D_2$ of FIG. 11), and in some instances 5.08 cm to 7.62 cm wide. Each strand can be divided into a plurality of sections of equal width (for example, $D_1=D_2=0.5$ cm). In some instances, each stand can be divided into a plurality of sections of unequal width ($D_1=0.5$ cm, $D_2=1$ cm, for example) The flat iron is preferably applied to each section of 7.62 cm in length at a time to maximize the frizz reduction. In some instances, the flat iron is applied to each section of between 10 cm and 15 cm in length at a time of each strand; and sometimes the flat iron is applied to each section of between 2.54 cm and 5.08 cm (e.g., section, $A_1$ and section $A_2$ shown in FIG. 11). In some instances, the hair can be treated by dividing each strand into a plurality of equal sections ($A_1=A_2=10$ cm, for example). In some other instances, the hair can be treated by dividing each strand into a plurality of sections having different length ($A_1=10$ cm and $A_2=15$ cm, for example).

The flat iron is used 3 to 10 times on each section of strand of hair. In some instances, 1-2 times if the hair has been already processed, heat damaged, or undergoing the second or third round of the hair-curl defining treatment. In some instances, each section is treated equal number of times (for example, section $A_1$ and $A_2$ are treated 5 times). According to another aspect of the present invention, each section can be treated different number of times (for example, section $A_1$ is treated 5 times and section $A_2$ is treated 10 times). The number of treatments depends on the tightness of curls and degree of frizz (the higher the tightness of curls and degree of frizz, the greater the number of times a particular section is treated). In some instances when a particular section comprises the hair that was previously relaxed, the treatment of this section is not needed (i.e., a section is not treated at all). The selection of temperatures is also dependent on the location of the hair in different parts of the head and on the tightness of the curls. Typically, the temperature for treatment of the hair of the nape is lower than that of the crown.

Figure 9:
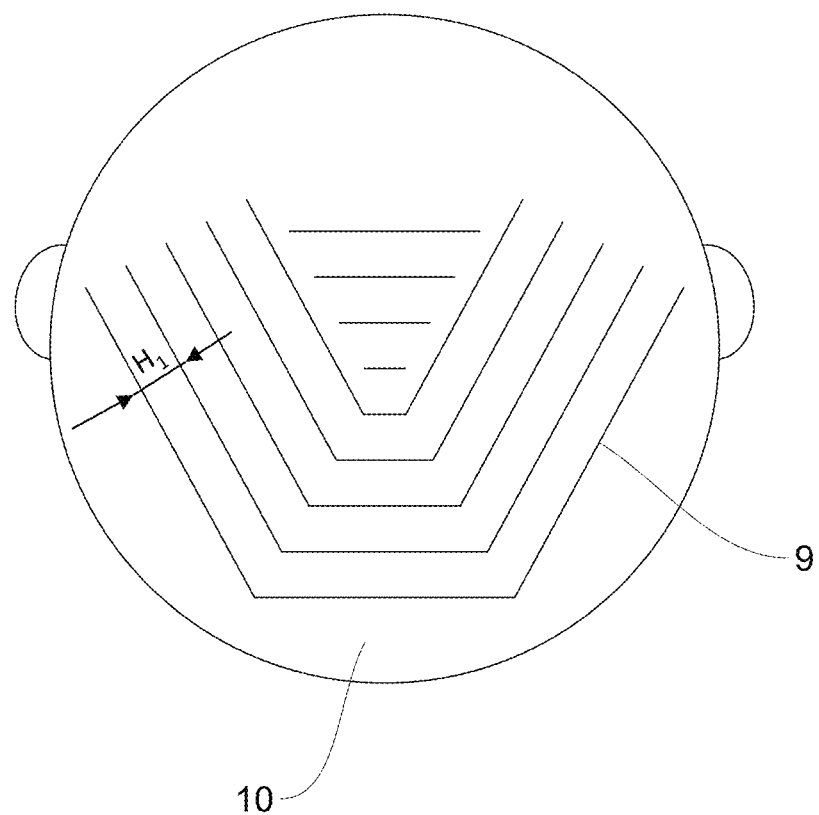
FIG. 9 is a top view of hair being treated horizontally and diagonally with the curl-hair defining method.
Figure 10:
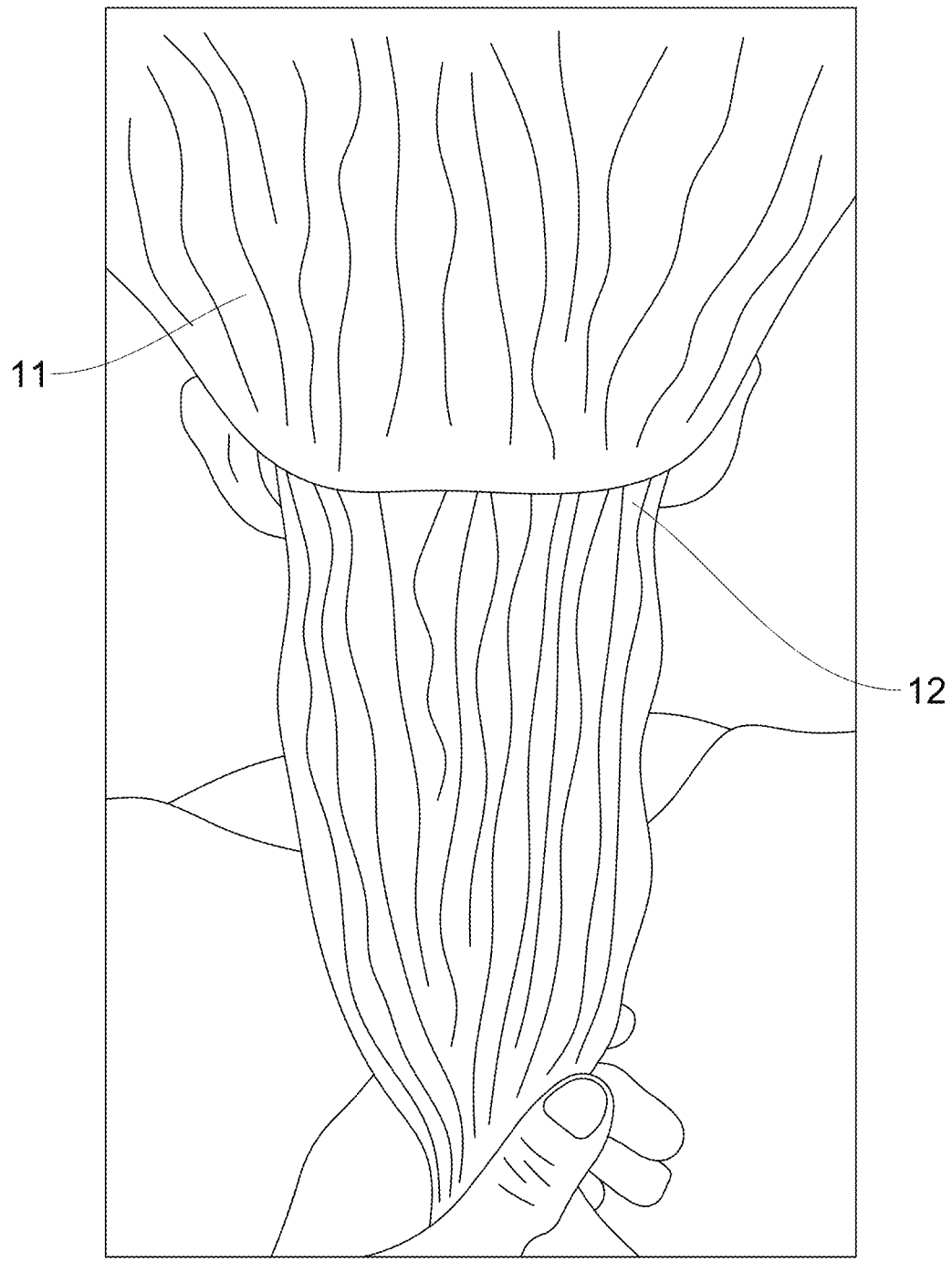
FIG. 10 is a side view of hair being treated horizontally with the curl-hair defining method.
Figure 11:
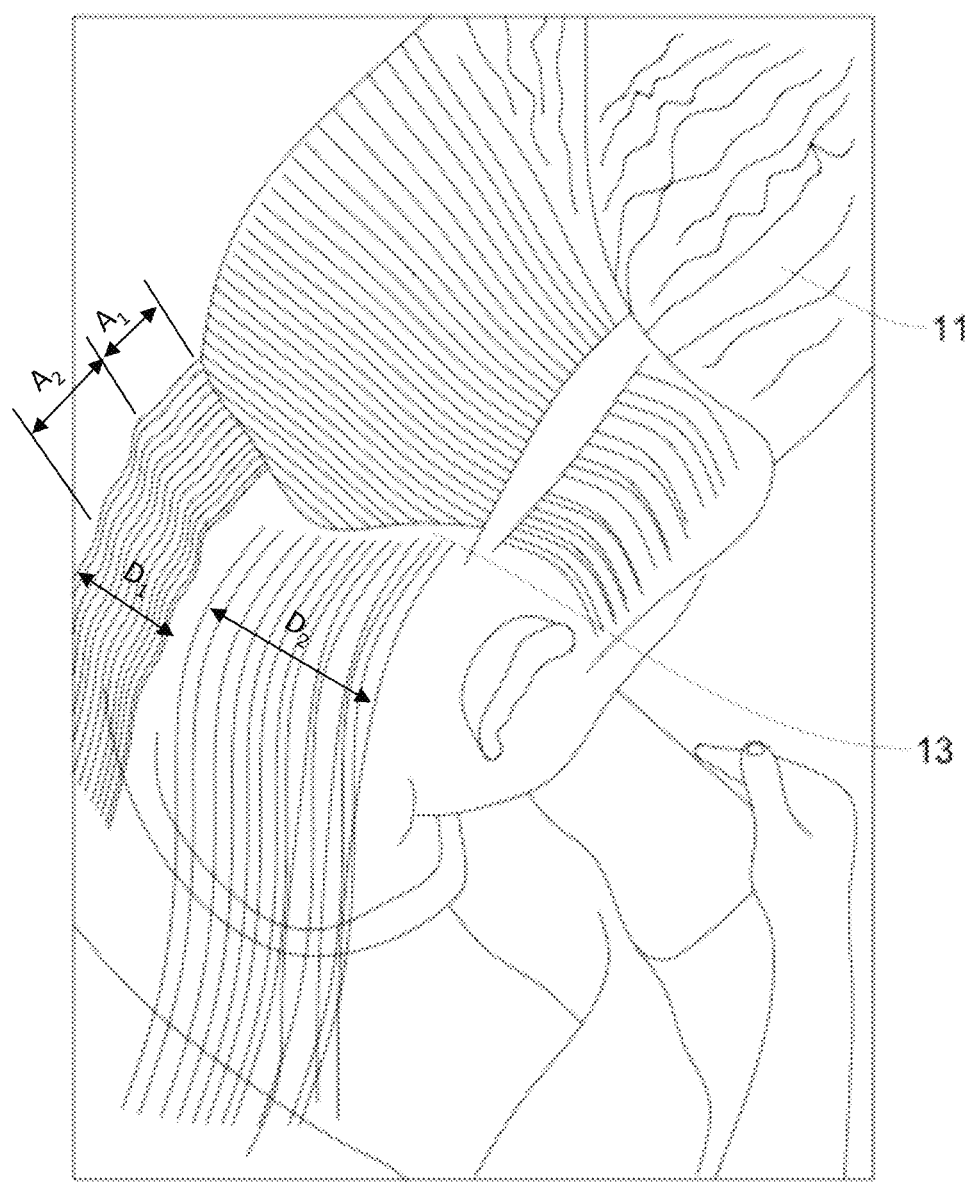
FIG. 11 is a side view of hair being treated diagonally with the curl-hair defining method.

In addition, the hair strands are treated by dividing a head into diagonal and horizontal subsections of 0.31 to 2.54 cm thick, and in some instances 0.63 cm to 1.27 cm thick. FIG. 9 demonstrates a top view of hair being treated by dividing a head into horizontal 10 and diagonal 9 subsections. The hair is divided in this manner to maximize frizz reduction, as well as to control and make all the different hair patterns as even as possible. In accordance with the method of the present invention, the thickness ($H_1$ of FIG. 9) for each subsection is also a function of the density of hair strands, wherein if the density of hair strands is high, the thickness of the subsection is lower; and conversely when the density of the hair strands is low, the thickness of the subsection is higher. In some instances, each subsection (horizontal and diagonal) can have the same thickness. Yet, in other instances, subsections can have different thickness, for example diagonal subsections 9 can have higher thickness than the horizontal subsections 10, or vice versa. And in some other instances, not all diagonal subsections can have the same thickness and similarly, not all horizontal subsections can have the same thickness. FIG. 10 is a side view of a person's hair 11 being treated horizontally parallel to separation line 12 with the curl-hair defining method and FIG. 11 is a side view of a person's hair 11 being treated diagonally parallel to separation line 13 with the curl-hair defining method.

Figure 3:
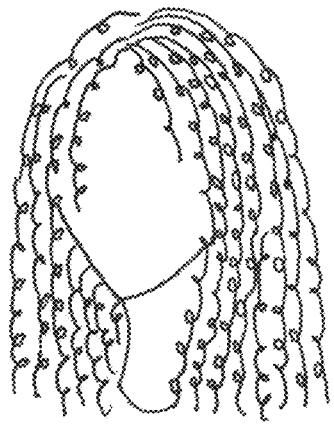
FIG. 3 depicts front views of four different types of hair: curly, coily, wavy, and loose
Figure 3:
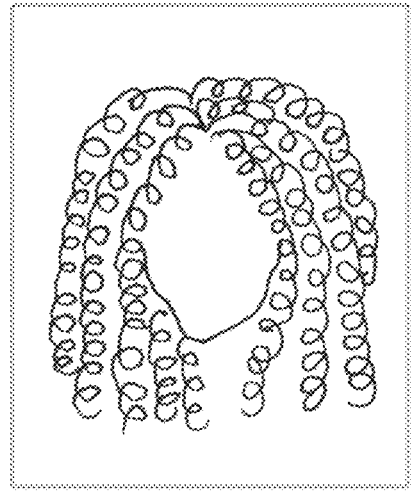
Figure 3:
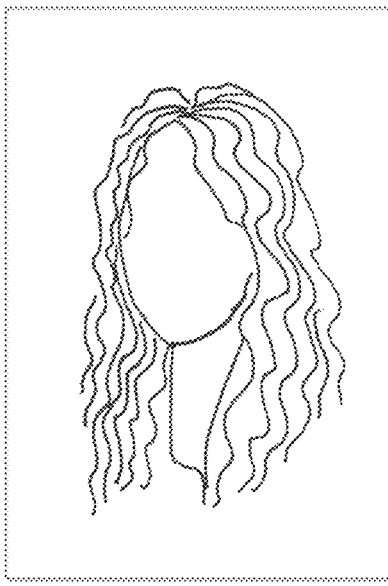
Figure 3:
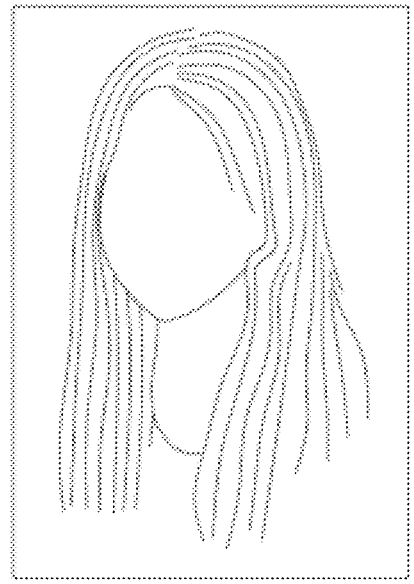
Figure 4:
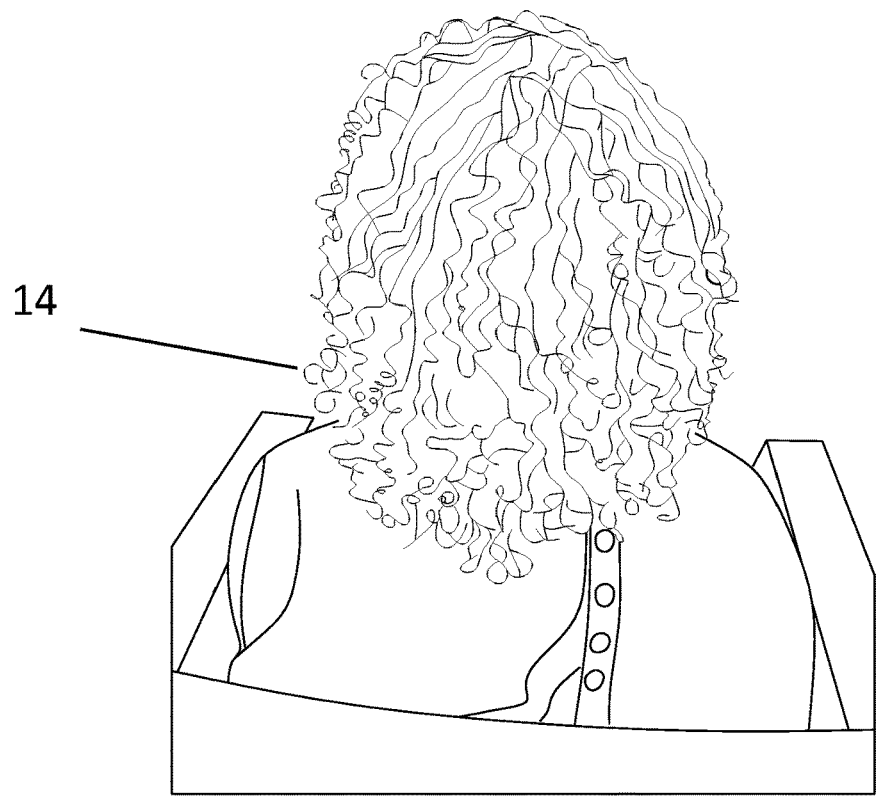
FIG. 4 depicts two individuals with different degrees of frizz, one individual has a low degree of frizz and the second individual has a high degree of frizz.
Figure 4:
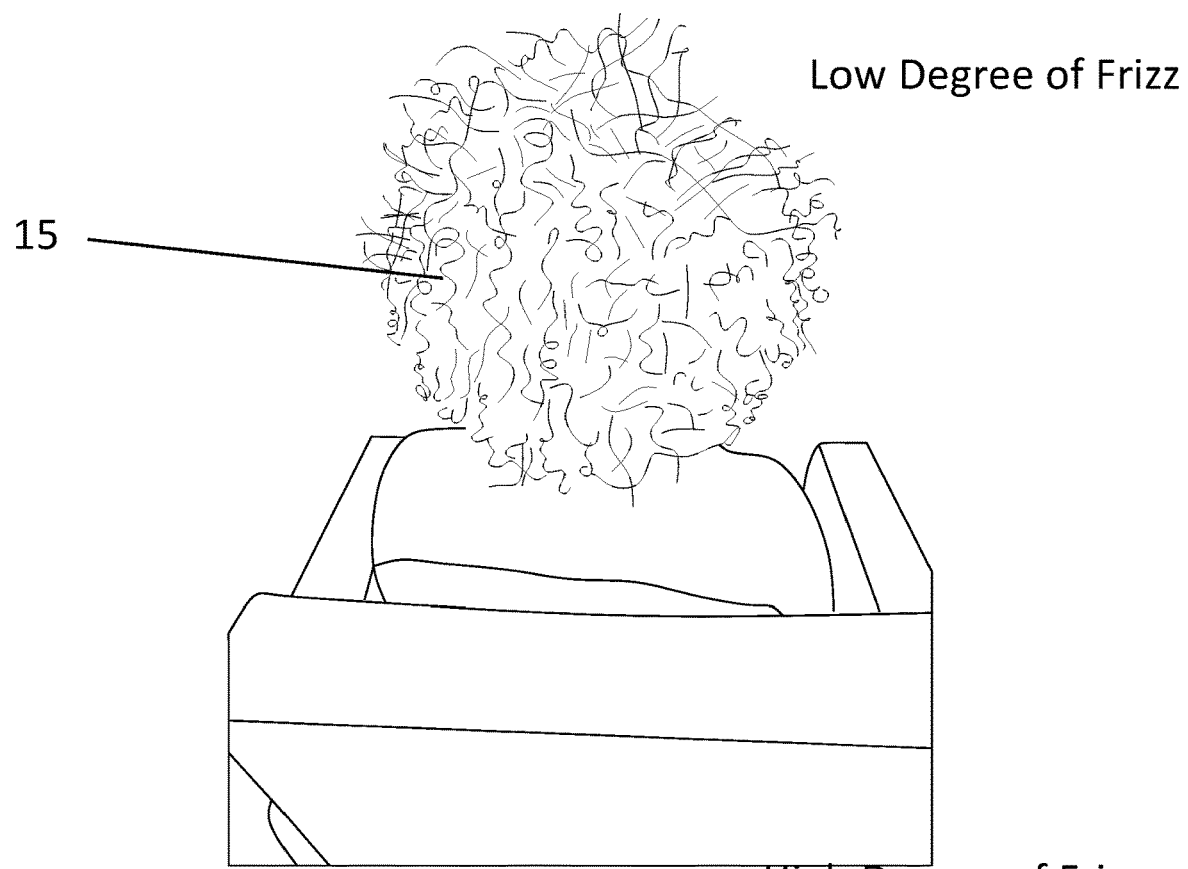

The temperature of the flat iron will depend on the specific hair type such as curly hair, coily hair, wavy hair, or loose hair, as shown in FIG. 3, for example and degree of frizz. The temperature of the flat iron will also depend on the amount of zigzag strands and different curl patterns, which are mixed and going in different directions, also on the amount of open cuticles. The degree of frizz as seen in FIG. 4 will depend on the number of cuticles that are open. When hair strands are going in the same direction, and cuticles are closed, the frizzy hair appears to be tamed 14 (characterized by a low degree of frizz, being unified and having an even s-shape). When strands are going in different directions, have many zigzag strands and have mixed curl patterns having more cuticles open, the frizzy hair of an individual appears untamable 15 (characterized by a high degree of frizz, being non-unified and having unruly hair shape, such as a zigzag shape, for example) as further illustrated in FIG. 7.

The temperature for coily hair is in the range of 210° C.-243° C., and in some instances is in the range of 232° C.-243° C. The temperature for wavy and curly hair is in the range of 176° C.-243° C., and in some instances is in the range of 187° C.-243° C., and yet in some other instances is in the range of 204° C.-216° C. The temperature for looser and bleached (processed) hair is in the range of 176° C.-210° C., in some instances is in the range of 188° C.-210° C., and yet in some other instances is in the range of 188° C.-199° C. The temperature for a low degree of frizz is in the range of 176° C.-216° C. and in some instances is in the range of 193° C.-216° C. The temperature for the high degree of frizz is in the range of 210° C.-243° C., and in some instances is in the range of 221° C.-243° C.

After application of the flat iron, the hair is rinsed and dried one more time before the second round of treatment begins.

Figure 2:
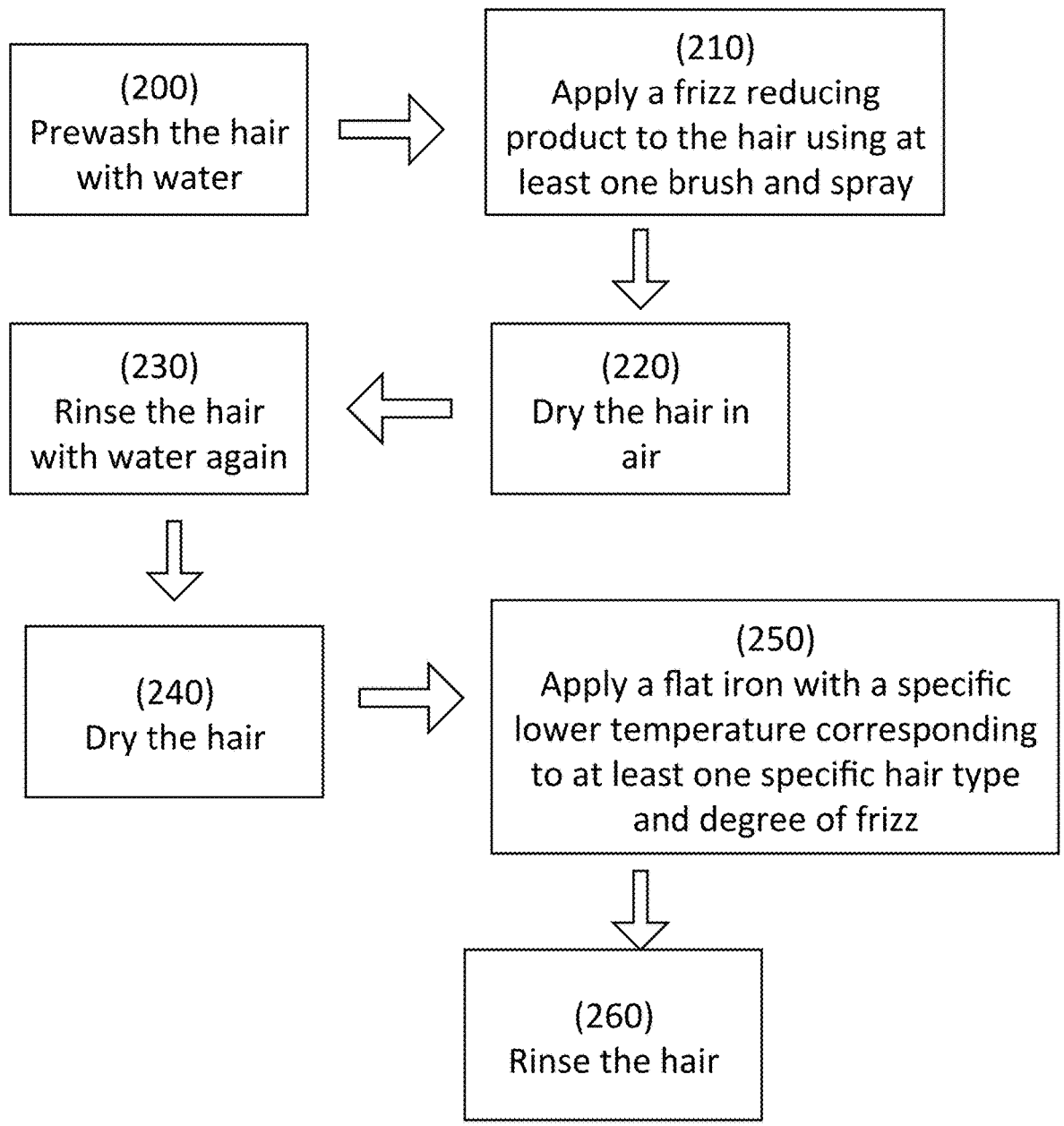
FIG. 2 depicts a flow chart which illustrates a series of steps for the second round of treatment to maximize the reduction of frizz in hair.

FIG. 2 demonstrates a series of steps to reduce frizz in a second round of treatment. This second round follows the same steps as the first round, but the flat iron temperatures are on the lower end in the second round of frizz reducing treatment. The steps for the second round of treating hair has the following steps: (200) prewashing the hair with water; (210) applying a frizz reducing product to the hair using at least one of a brush and a spray, (220) drying the hair in air, (230) rinsing the hair with water again, (240) drying the hair, (250) applying a flat iron with a specific temperature corresponding to at least one of specific hair type and degree of frizz; and (260) rinsing the hair again.

In the second round of treatment the temperature for coily hair is in the range of 204° C.-243° C., and in some instances is in the range of 204° C.-227° C., the temperature for wavy and curly hair is in the range of 177° C.-210° C., and in some instances is in the range of 177° C.-199° C., and the temperature for looser and bleached (processed) hair is in the range of 160° C.-210° C., and in some instances is in the range of 160° C.-182° C. The temperature for a low degree of frizz is in the range of 160° C.-210° C., and in some instances is in the range of 160° C.-199° C. and the temperature for the high degree of frizz is in the range of 193° C.-240° C., and in some instances is in the range of 193° C.-227° C.

After the second round of treatment is complete, styling product can be additionally applied to further reduce frizz such as a styling product, a shaping-up product, shampoo, or conditioner, or a combination of styling products. These additional products are used to further enhance the results of the curl-hair defining method.

According to another aspect of the present invention, a third round of treatment can be used after the second round of treatment, especially when the hair is very tight and frizzy. In the third round of treatment the temperature for coily hair is in the range of 204° C.-243° C., and in some instances is in the range of 204° C.-227° C., the temperature for wavy and curly hair is in the range of 177° C.-210° C., and in some instances is in the range of 177° C.-199° C., and the temperature for looser and bleached (processed) hair is in the range of 160° C.-210° C., and in some instances is in the range of 160° C.-182° C. The temperature for a low degree of frizz is in the range of 160° C.-210° C., and in some instances is in the range of 160° C.-199° C. and the temperature for the high degree of frizz is in the range of 193° C.-240° C., and in some instances is in the range of 193° C.-227° C. The application of the third round of treatment will result in the hair characterized by the best definition and transformation.

Figure 5:
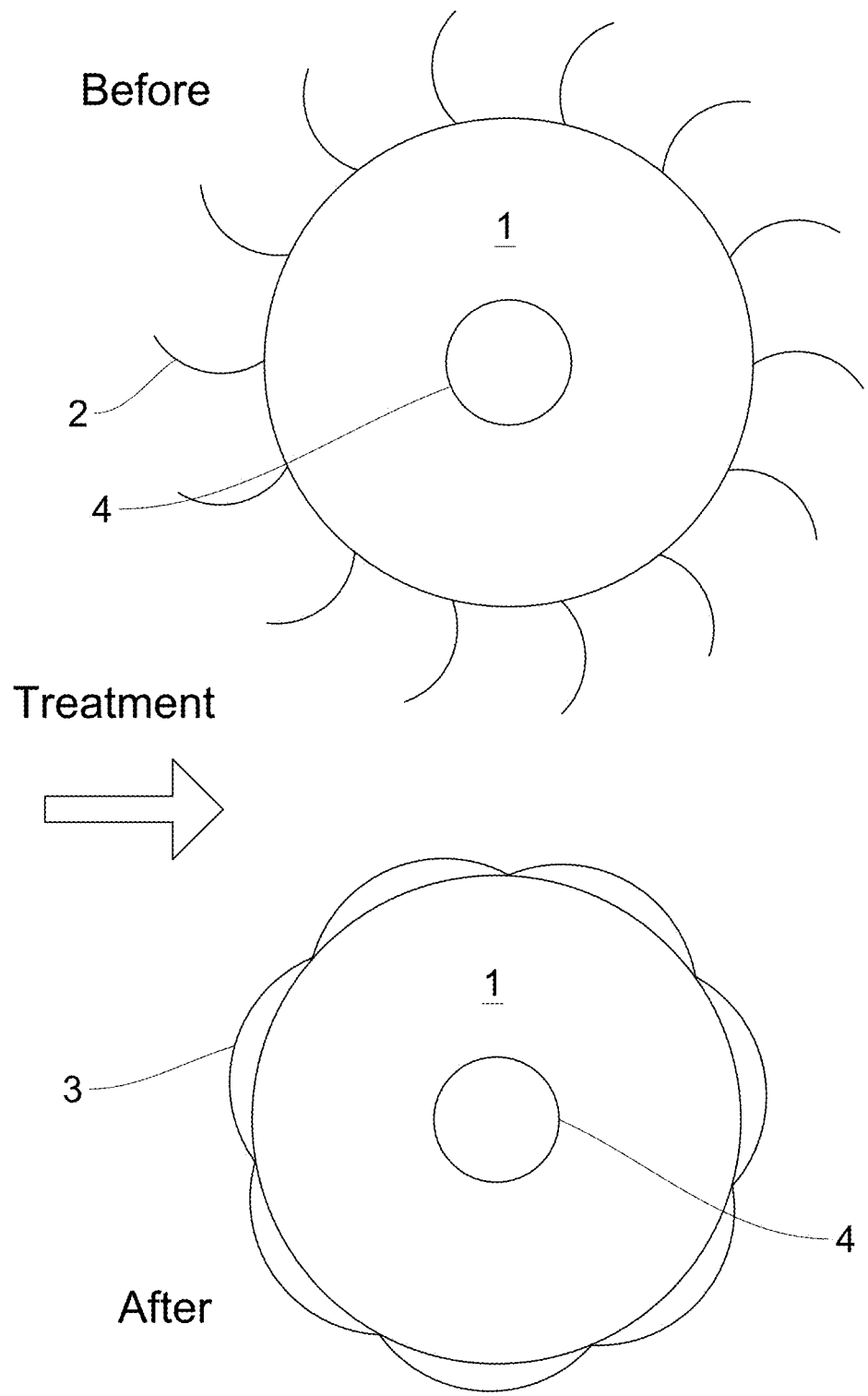
FIG. 5 is a top view of a cuticle before and after application of the curl-hair defining method.
Figure 7:
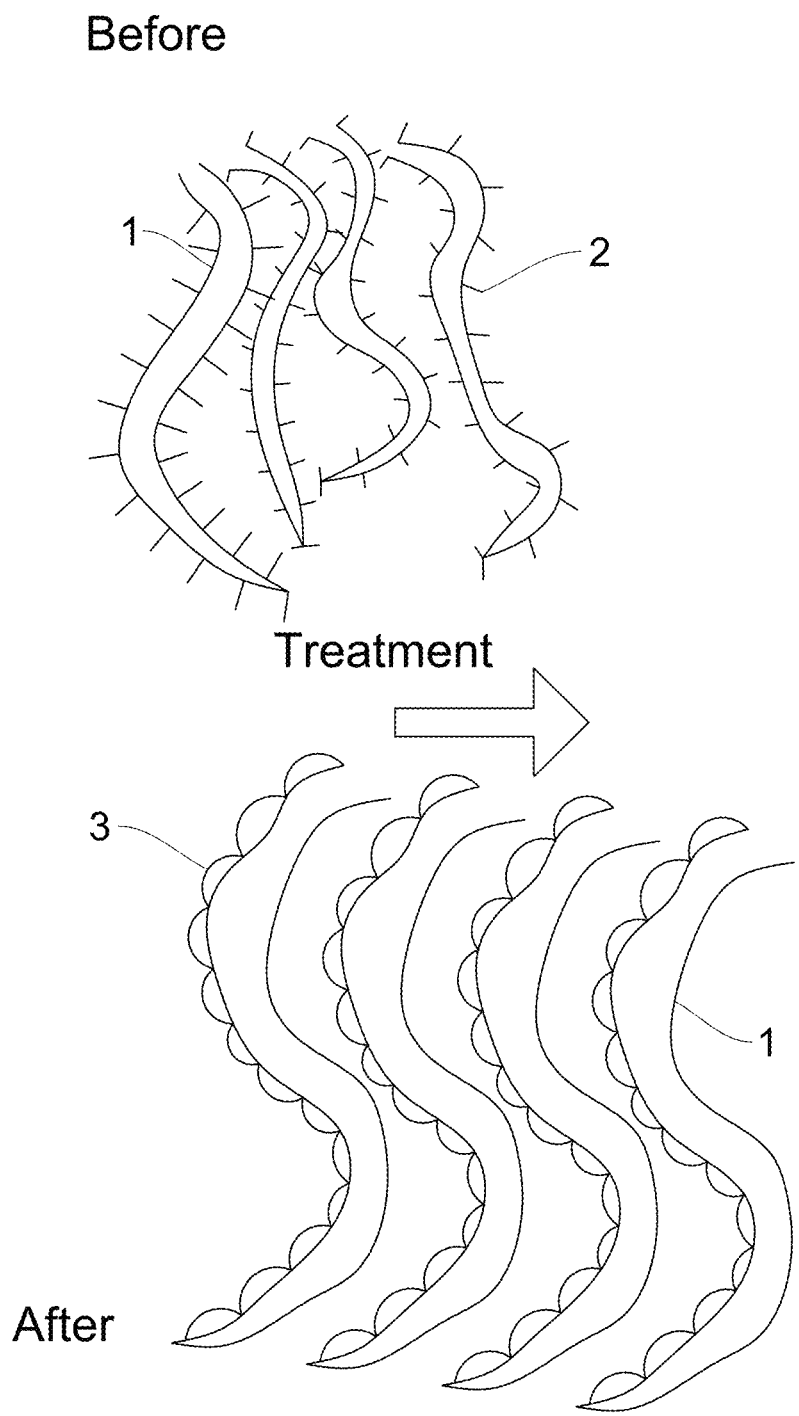
FIG. 7 is a view of hair with open cuticles and hair with closed cuticles after application of the curl-hair defining method.

FIG. 5, there is shown a top view of a cuticle before and after application of the curl-hair defining method. Prior to treatment the cuticle 2 is open. The cortex 1 (and in some instances, medulla 4) is more susceptible to damage. The cuticle is dry and has high porosity. After the treatment, the cuticle 3 is closed and shiny. As a result, the closed cuticle 3 has a shiny and vibrant appearance. FIG. 7 shows the same hair cuticle at a front view before and after application of the curl-hair defining method. The hair strands are unruly with sharp edges turning and going into different directions (1). The hair is unmanageable with open cuticles (2) prior to the treatment, and after the treatment the frizzy strands loosen and unify to make defined strands, wherein the hair strands are laying loose and going in the same direction thereby creating a unified S-shape pattern (3).

Figure 6:
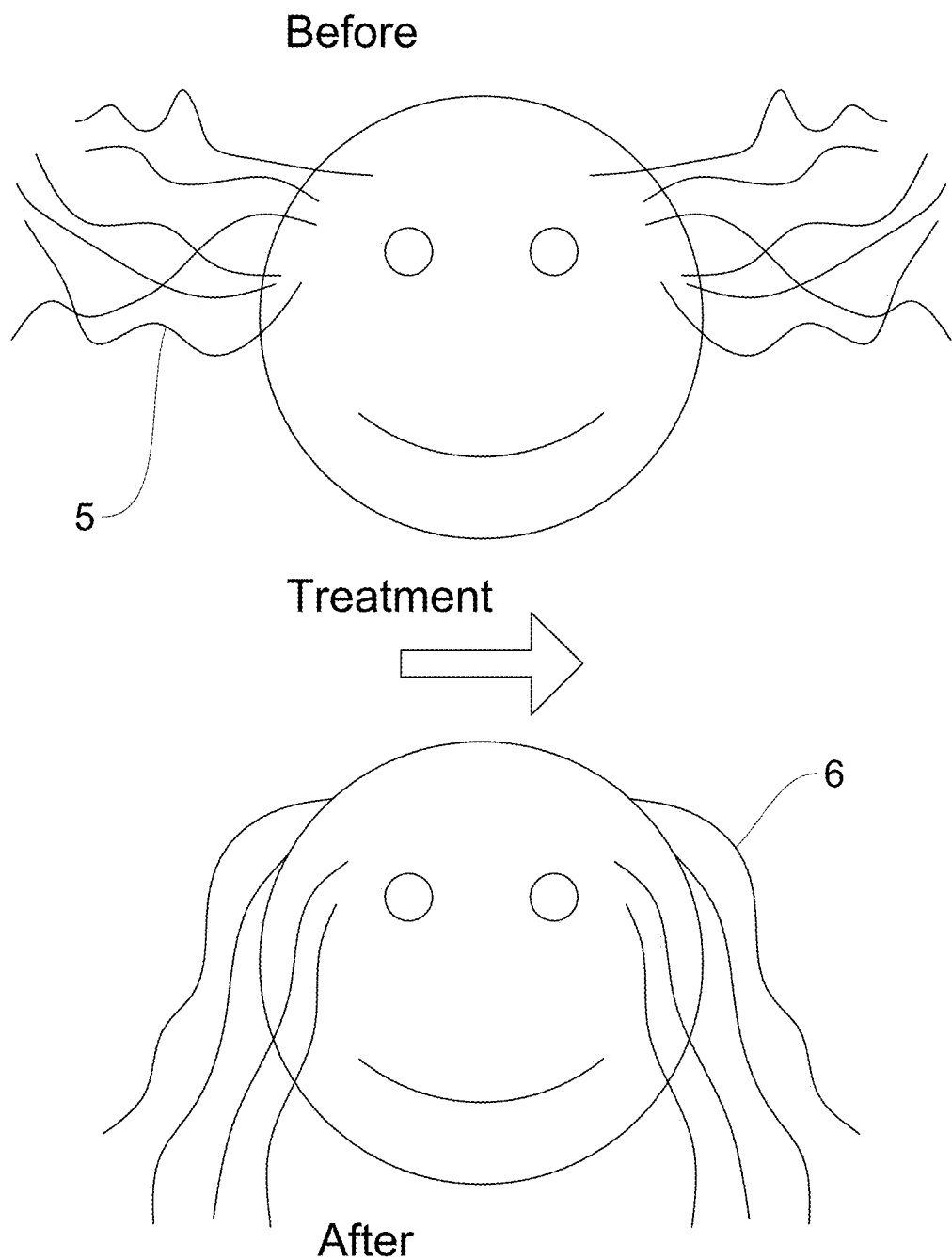
FIG. 6 is a side view of hair before and after application of the curl-hair defining method.
Figure 8A:
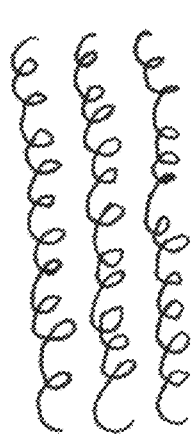
FIG. 8A is an illustration of curly hair before and after application of the curl-hair defining method.
Figure 8A:
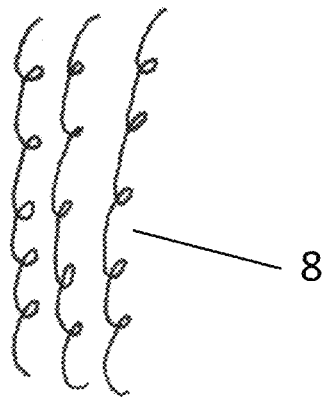
Figure 8B:
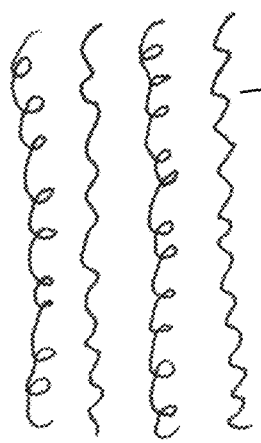
FIG. 8B is an illustration of a combination of curly and wavy hair before and after application of the curl-hair defining method.
Figure 8B:
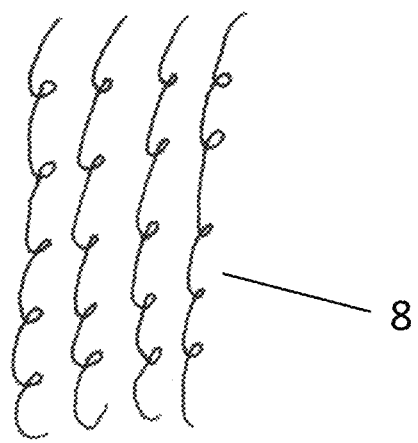

In some instances, an individual will have curly hair as can be seen in FIG. 8A or a combination of wavy and curly hair as shown in FIG. 8B. FIG. 8A is an illustration of curly hair before and after application of the curl-hair defining method. Although the composition and appearance of curly hair is different than other types of hair, the results are the same (as in the case of a combination of curly and wavy hair as shown in FIG. 8B, for example), curly hair starts as unmanageable and frizzy 7 and then becomes loose and unified 8, resulting in 30%-40% reduction in a number of curls (i.e., reduction in curliness), looking healthy, being bouncy as well as retaining s-shape. FIG. 6 shows the condition of hair before (5) and after (6) the treatment with noticeable differences in the appearance of the hair.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

Although the invention is described herein with reference to specific embodiments, various modifications and changes can be made without departing from the scope of the present invention as set forth in the claims below. Accordingly, the specification and figures are to be regarded in an illustrative rather than a restrictive sense, and all such modifications are intended to be included within the scope of the present invention. Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements.

The foregoing detailed description is merely exemplary in nature and is not intended to limit the invention or application and uses of the invention. Furthermore, there is no intention to be bound by any expressed or implied theory presented in the preceding technical field, background, brief summary, or the following detailed description.

What is claimed is:

1. A method of treating hair to reduce a frizz comprising the steps of:
   prewashing the hair with water;
   applying a frizz reducing product to the hair using at least one of a brush and a spray, wherein the frizz reducing product is comprised of glyoxylic acid and mildly acidic being composed of a solution with a pH ranging from 0.08-3.0;
   drying the hair in air; wherein the duration of drying the hair in the air is between 10 minutes and 20 minutes;
   rinsing the hair with water;
   drying the hair;
   applying to the hair a flat iron with a specific temperature corresponding to curly hair, coily hair, wavy hair and loose hair and degree of frizz; wherein the temperature for coily hair is in the range of 210° C.-243° C.; wherein the temperature for wavy and curly hair is in the range of 176° C.-243° C.; wherein the temperature for loose hair is in the range of 176° C.-210° C.; wherein the temperature for a low degree of frizz is in the range of 176° C.-216° C. and the temperature for the high degree of frizz is in the range of 210° C.-243° C.; and
   wherein the hair is separated into strands, wherein each strand is treated between 10 cm and 15 cm in length at a time, 3 to 10 times; and wherein the hair strands are treated by dividing a head into diagonal and horizontal sections of 0.31 cm to 2.54 cm in thickness and rinsing the hair with water after application of flat iron and drying the hair.

2. The method of claim 1, wherein the hair is separated into strands, and wherein each strand to be treated is approximately 1.27 cm to 10.16 cm wide.

3. The method of claim 1 wherein the step of applying to the hair a flat iron is performed by resting the hair in between the heated sides of the flat iron and moving the flat iron down.

* * * * *